(12) United States Patent
Delfort et al.

(10) Patent No.: US 9,211,495 B2
(45) Date of Patent: Dec. 15, 2015

(54) ABSORBENT SOLUTION CONTAINING A BREAKDOWN INHIBITOR DERIVED FROM PYRIMIDINE OR FROM TRIAZINE AND ABSORPTION PROCESS FOR ACID COMPOUNDS CONTAINED IN A GASEOUS EFFLUENT

(75) Inventors: Bruno Delfort, Paris (FR); P-Louis Carrette, Lyons (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 571 days.

(21) Appl. No.: 13/512,695

(22) PCT Filed: Nov. 19, 2010

(86) PCT No.: PCT/FR2010/000775
§ 371 (c)(1),
(2), (4) Date: Aug. 7, 2012

(87) PCT Pub. No.: WO2011/064470
PCT Pub. Date: Jun. 3, 2011

(65) Prior Publication Data
US 2012/0292565 A1    Nov. 22, 2012

(30) Foreign Application Priority Data

Nov. 30, 2009   (FR) ...................................... 09 05753

(51) Int. Cl.
| | | |
|---|---|---|
| *B01D 53/14* | (2006.01) | |
| *C07C 211/14* | (2006.01) | |
| *C07C 215/08* | (2006.01) | |
| *C07C 215/10* | (2006.01) | |
| *C07C 229/08* | (2006.01) | |
| *C07C 309/14* | (2006.01) | |

(52) U.S. Cl.
CPC ........ *B01D 53/1493* (2013.01); *B01D 53/1456* (2013.01); *C07C 211/14* (2013.01); *C07C 215/08* (2013.01); *C07C 215/10* (2013.01); *C07C 229/08* (2013.01); *C07C 309/14* (2013.01); *B01D 2252/103* (2013.01); *B01D 2252/20405* (2013.01); *B01D 2252/20421* (2013.01); *B01D 2252/20484* (2013.01); *B01D 2252/604* (2013.01); *B01D 2257/302* (2013.01); *B01D 2257/304* (2013.01); *B01D 2257/306* (2013.01); *B01D 2257/308* (2013.01); *B01D 2257/404* (2013.01); *B01D 2257/504* (2013.01); *B01D 2258/0233* (2013.01); *B01D 2258/0291* (2013.01); *B01D 2258/05* (2013.01)

(58) Field of Classification Search
CPC .............. C07D 215/08; C07D 239/38; B01D 2252/20484; B01D 53/1493
USPC .................................. 252/190, 373; 423/210
See application file for complete search history.

(56) References Cited

U.S. PATENT DOCUMENTS

| | | | |
|---|---|---|---|
| 2,655,543 A | | 10/1953 | Linch |
| 3,133,858 A | * | 5/1964 | Hartop, Jr. et al. ........... 514/271 |
| 7,186,753 B1 | * | 3/2007 | Del Soldato .................. 514/509 |
| 2005/0202967 A1 | | 9/2005 | Hoefer et al. |

FOREIGN PATENT DOCUMENTS

| | | |
|---|---|---|
| WO | WO 99/10561 | 3/1999 |
| WO | WO 2009/156619 | 12/2009 |

OTHER PUBLICATIONS

Malmgren, H., et al., "A large scale process for the preparation of thymitaq," Organic Process Research & Development, 2008, 12, 1195-1200.*
Kohl et al., Mechanical Design and Operation of Ethanolamine Plants, Gas Purification, Third Edition, Jan. 1, 1979, pp. 91-123.
Butwell et al., Alkanolamine Treating, Hydrocarbon Processing, No. 3, Mar. 1, 1982, pp. 108-116.
Search Report of PCT/FR2010/000775 dated Feb. 22, 2011.

* cited by examiner

*Primary Examiner* — Liam J Heincer
*Assistant Examiner* — Nicholas Hill
(74) *Attorney, Agent, or Firm* — Fitch, Even, Tabin and Flannery LLP

(57) ABSTRACT

The degradation of an absorbent solution comprising organic compounds provided with an amine function in aqueous solution is reduced considerably in the presence of a small amount of degradation-inhibiting additives belonging to the class of derivatives of pyrimidine or of triazine, at least one substituent of which contains a sulfur atom.
The absorbent solution is employed for deacidifying a gaseous effluent.

16 Claims, 1 Drawing Sheet

Figure 1:
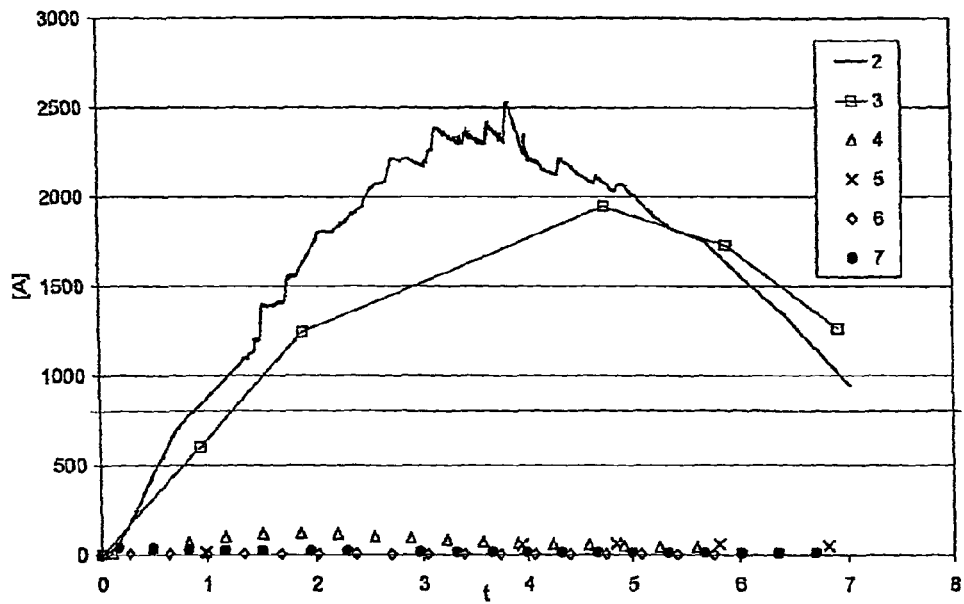

ABSORBENT SOLUTION CONTAINING A BREAKDOWN INHIBITOR DERIVED FROM PYRIMIDINE OR FROM TRIAZINE AND ABSORPTION PROCESS FOR ACID COMPOUNDS CONTAINED IN A GASEOUS EFFLUENT

The present invention relates to the field of deacidification of a gaseous effluent. More precisely the present invention proposes compounds for reducing the degradation of an absorbent solution employed for absorbing the acidic compounds contained in a gaseous effluent, the absorbent solution comprising amines in aqueous solution. In particular, the invention relates to compounds used for reducing the degradation of the amines used for the deacidification of gases containing oxygen, for example flue gas.

The deacidification of gaseous effluents, such as natural gas and flue gas for example, is generally carried out by scrubbing with an absorbent solution. The absorbent solution makes it possible to absorb the acidic compounds present in the gaseous effluent ($H_2S$, mercaptans, $CO_2$, COS, $SO_2$, $CS_2$).

The deacidification of these effluents, notably decarbonation and desulfurization, imposes specific constraints on the absorbent solution, in particular thermal and chemical stability notably in the presence of the impurities of the effluent, i.e. essentially oxygen, SOx and NOx. Oxygen can also come into contact with the absorbent solution without necessarily being present in the gaseous effluent to be treated, as in the case for example of accidental ingress of air at the absorbent solution storage tanks.

The absorbent solutions most used at present are aqueous solutions of alkanolamines. We may mention document FR 2 820 430, which proposes methods for deacidifying gaseous effluents.

However, a person skilled in the art is well aware that these amines have the drawback that they undergo degradation in the service conditions.

In particular, the amines can be degraded by oxygen, causing consumption of the amine and the formation of degradation products, which accumulate in the unit or, for the most volatile products, are entrained in the gaseous effluents from the process. Thus, especially in the case of post-combustion treatment of flue gas in a method using an aqueous solution of monoethanolamine (MEA), large amounts of ammonia are formed. The ammonia thus formed is entrained into the atmosphere with the treated flue gas, which poses problems with respect to protection of the environment.

In the case of capture of the $CO_2$ in the flue gases from industrial units or from production of electricity or of energy in general, the phenomena of degradation of the absorbent solution based on amines are increased by the presence of a massive amount of oxygen in the feed to be treated, which can generally be up to 5 vol. %. In the case of flue gas from the natural gas combined cycle, the content of oxygen by volume in the flue gas can reach 15%.

The degraded solution is characterized by:
 a decrease in absorption of the acidic compounds in the feed relative to a fresh amine solution,
 an increase in the density of the absorbent solution, as well as its viscosity, which can lead to a loss of performance,
 formation of more-volatile amines that contaminate the treated gas and the acidic gas from the regeneration step: ammonia, methylamine, dimethylamine and trimethylamine for example, depending on the nature of the amine used,
 accumulation of degradation products in the absorbent solution, which may necessitate treatment of the degraded solution,
 possible problems with foaming due to the degradation products.

The degradation of the absorbent solution therefore affects the performance and proper functioning of the gas deacidification units.

To overcome the problem of degradation, if it is not possible to limit or eliminate the presence of oxygen in the absorbent solution, compounds are added to the absorbent solution whose role is to prevent or limit the phenomena of degradation of the amine compounds, notably the degradation caused by oxidation phenomena. These compounds are commonly called degradation-inhibiting additives. The principal known modes of action of the degradation-inhibiting additives consist, depending on their nature, of a reaction of the reduction type and/or of capture, trapping and/or stabilization of the radicals formed in the absorbent solution in order to limit or prevent or interrupt the reactions, notably the chain reactions, of degradation.

U.S. Pat. No. 5,686,016 mentions additives used for limiting the degradation of absorbent solutions used for the deacidification of natural gas, in particular oximes.

U.S. Pat. No. 7,056,482 mentions additives used for limiting the degradation of absorbent solutions used for capture of $CO_2$, in particular thiosulfates and sulfites.

In general, the present invention proposes a class of degradation-inhibiting additives that is notably able to reduce the degradation of an absorbent solution employed for absorption of the acidic compounds contained in a gaseous effluent, said absorbent solution comprising amine compounds in aqueous solution.

The present invention describes an absorbent solution for absorbing the acidic compounds of a gaseous effluent, said solution comprising:
 a) at least one amine,
 b) water,
 c) at least one degradation-inhibiting compound for limiting the degradation of said amine, said degradation-inhibiting compound corresponding to one of the following general formulas:

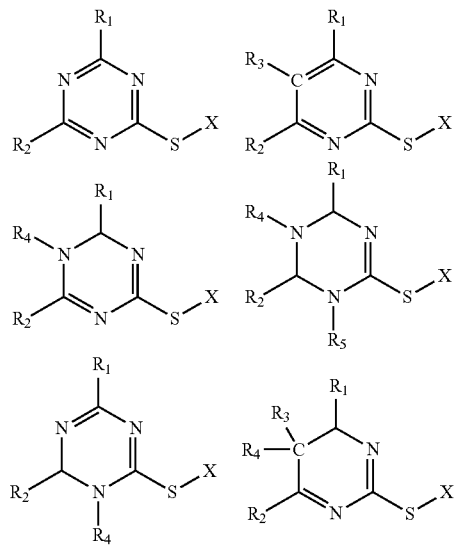

-continued

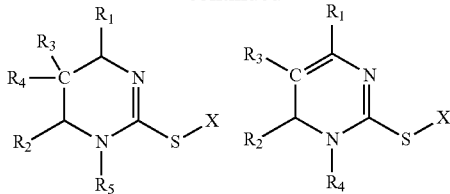

in which X is selected from
  a hydrogen atom,
  an alkali or alkaline-earth element,
  a monovalent or multivalent metal,
  an ammonium cation $NH_4^+$ or one resulting from the protonation of an amine function,
  a phosphonium cation,
in which each of the radicals $R_1$, $R_2$ and $R_3$ is selected independently from:
  a hydrogen atom,
  a hydrocarbon radical comprising 1 to 12 carbon atoms,
  a radical

in which W is selected from a sulfur atom and an oxygen atom and Y is selected from:
  a hydrogen atom,
  a hydrocarbon radical comprising 1 to 12 carbon atoms,
  an alkali or alkaline-earth element,
  a monovalent or multivalent metal,
  an ammonium cation $NH_4$ or one resulting from the protonation of an amine function,
  a phosphonium cation,
and in which each of the radicals $R_4$ and $R_5$ is selected independently from:
  a hydrogen atom,
  a hydrocarbon radical comprising 1 to 12 carbon atoms.

At least one of the radicals $R_1$, $R_2$, $R_3$, X and Y can be a hydrocarbon group containing between 1 and 12 carbon atoms and can further contain at least one compound selected from a heteroatom and a halogen.

At least one of the radicals $R_1$, $R_2$, $R_3$, X and Y can be a hydrocarbon group containing between 1 and 12 carbon atoms and can further comprise at least one function selected from the group: a hydroxyl function, a ketone function, a carboxyl function and a nitrile function.

The solution can comprise between 10 and 99 wt. % of amine, between 1 and 90 wt. % of water and between 5 ppm and 5 wt. % of degradation-inhibiting compound.

The degradation-inhibiting compound can be selected from the group containing: 2-thiouracil (or 4-hydroxy-2-mercaptopyrimidine), a salt of 2-thiouracil (or 4-hydroxy-2-mercaptopyrimidine), 4-thiouracil (or 2-hydroxy-4-mercaptopyrimidine), a salt of 4-thiouracil (or 2-hydroxy-4-mercaptopyrimidine), 2-thiobarbituric acid (or 4,6-dihydroxypyrimidine-2-thiol), a salt of 2-thiobarbituric acid (or 4,6-dihydroxypyrimidine-2-thiol), 2-mercaptopyrimidine, a salt of 2-mercaptopyrimidine, 3,4,5,6-tetrahydropyrimidine-2-thiol, a salt of 3,4,5,6-tetrahydropyrimidine-2-thiol, 4,5-dihydro-4,4,6-trimethyl-2-pyrimidinethiol, a salt of 4,5-dihydro-4,4,6-trimethyl-2-pyrimidinethiol, 4-hydroxy-2-mercapto-6-methylpyrimidine, a salt of 4-hydroxy-2-mercapto-6-methylpyrimidine, 2-mercapto-4-methylpyrimidine, a salt of 2-mercapto-4-methylpyrimidine, 1,3,5-triazine-2,4,6-trithiol, a salt of 1,3,5-triazine-2,4,6-trithiol, and 4-methyl-2-(methylthio)pyrimidine.

The amine can be selected from the group containing: N,N,N',N',N''-pentamethyldiethylenetriamine, piperazine, monoethanolamine, diethanolamine, methyldiethanolamine, diisopropanolamine, diglycolamine, a glycine salt and a taurine salt.

In the case when the amine is monoethanolamine, the degradation-inhibiting compound is selected from 2-thiobarbituric acid, 2-thiouracil, 3,4,5,6-tetrahydro-2-pyrimidinethiol and the sodium triple salt of 1,3,5-triazine-2,4,6-trithiol.

The absorbent solution according to the invention can comprise at least 39 wt. % of monoethanolamine.

The invention also describes a method of absorbing acidic compounds contained in a gaseous effluent, in which the gaseous effluent is contacted with an absorbent solution according to the invention as described above.

In the method according to the invention, the aqueous solution can be used for absorbing acidic compounds contained in one of the effluents of the group containing natural gas, flue gas, synthesis gases, refinery gases, the gases obtained at the end of the Claus process, gases from fermentation of biomass, gases from cement works and incinerator flue gas.

The gaseous effluent can comprise at least 500 ppm of oxygen by volume.

Figure 2:
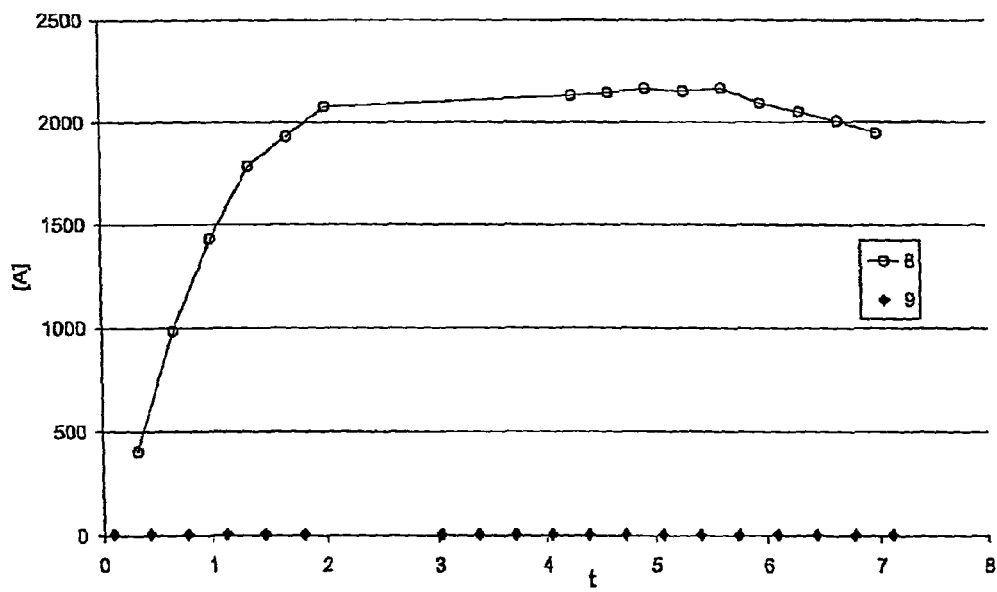

Other features and advantages of the invention will be more easily understood and will become clearer on reading the description given hereunder, referring to the appended drawings in which FIGS. 1 and 2 show the $NH_3$ content in the gas treated with an absorbent solution, depending on whether or not degradation-inhibiting additives were added to the absorbent solution and as a function of the amine content of the absorbent solution.

In order to reduce the degradation of an absorbent solution, the inventors showed that the degradation of an absorbent solution comprising organic compounds provided with an amine function in aqueous solution is reduced considerably in the presence of a small amount of degradation-inhibiting additives described below.

The degradation-inhibiting additives according to the invention are compounds belonging to the class of derivatives of pyrimidine or of triazine, at least one substituent of which contains a sulfur atom.

In the present description, pyrimidine means the 6-atom cyclic compounds whose ring comprises 4 carbon atoms and 2 nitrogen atoms in position 1 and 3, and 3 unsaturations, and triazine means a 6-atom cyclic compound whose ring comprises 3 nitrogen atoms, 3 carbon atoms and 3 unsaturations.

In the present description, derivatives of pyrimidine, at least one substituent of which contains a sulfur atom, means that at least one of the carbon atoms of the pyrimidine ring is bound to a sulfur atom.

In the present description, derivatives of triazine, at least one substituent of which contains a sulfur atom, means that at least one of the carbon atoms of the triazine ring is bound to a sulfur atom.

The degradation-inhibiting compounds according to the invention can for example correspond to the following general formula:

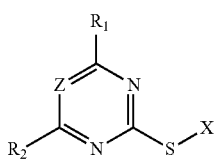
(formula I)

Z is such that the unit

is:
a unit

and in this case general formula I becomes

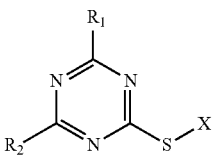
(formula II)

Formula II corresponds to a triazine derivative, at least one substituent of which contains a sulfur atom,
a unit

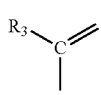

and in this case the general formula becomes:

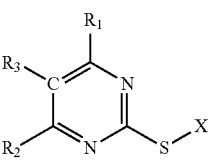
(formula III)

Formula III corresponds to a pyrimidine derivative, at least one substituent of which comprises a sulfur atom.
In formulas I, II and III, X is selected from:
  a hydrogen atom,
  an alkali or alkaline-earth element,
  a monovalent or multivalent metal,
  an ammonium cation $NH_4^+$ or a cation resulting from the protonation of an amine function,
  a phosphonium cation,
  a saturated or unsaturated, linear, branched or cyclic, heterocyclic or aromatic hydrocarbon radical comprising 1 to 12 carbon atoms, that can optionally be joined to heteroatoms, halogens, and can contain hydroxyl, ketone, carboxyl or nitrile functions.

In the case when X is a multivalent element, it is understood that for neutrality of the molecule, it can take the form

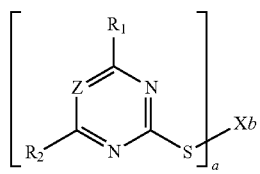

where a and b are integers allowing observance of neutrality or valences complying with the rules of chemistry.
In formulas I, II and III, $R_1$, $R_2$ and $R_3$ are selected indiscriminately from:
  a hydrogen atom,
  a saturated or unsaturated, linear, branched or cyclic, heterocyclic or aromatic hydrocarbon radical comprising 1 to 12 carbon atoms that can optionally be joined to heteroatoms, halogens, and can contain hydroxyl, ketone, carboxyl or nitrile functions,
  a radical

with W being a sulfur atom or an oxygen atom
and Y being selected from:
  a hydrogen atom,
  a saturated or unsaturated, linear, branched or cyclic, heterocyclic or aromatic hydrocarbon radical comprising 1 to 12 carbon atoms, that can optionally be joined to heteroatoms, halogens, and can contain hydroxyl, ketone, carboxyl or nitrile functions,
  an alkali or alkaline-earth element,
  a monovalent or multivalent metal,
  an ammonium $NH_4^+$ cation or one resulting from the protonation of an amine function,
  a phosphonium cation.

General formula II can also extend to the partially hydrogenated forms that can take the following forms:

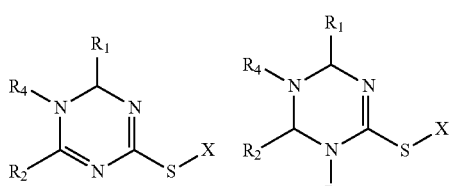

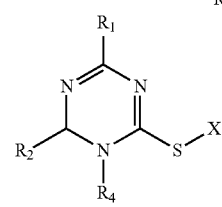

General formula III can also extend to the partially hydrogenated forms that can take the following forms:

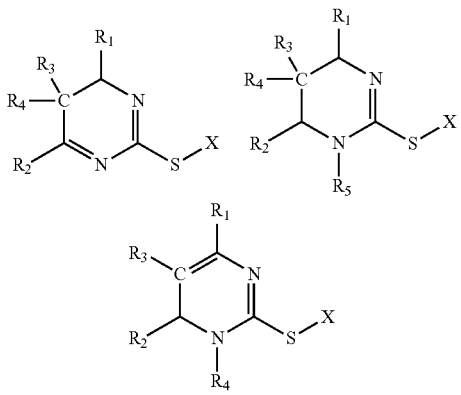

in which $R_4$ and $R_5$ are selected from a hydrogen atom or a radical comprising 1 to 12 carbon atoms, saturated or unsaturated, linear, branched or cyclic, heterocyclic or aromatic.

The molecules of the invention can also exist in their so-called tautomeric form when allowed, and complying with the rules of organic chemistry.

The absorbent solutions according to the invention can be used for deacidifying the following gaseous effluents: natural gas, synthesis gases, flue gas, refinery gases, gases obtained at the end of the Claus process, gases from fermentation of biomass, gases from cement works, incinerator flue gas. These gaseous effluents contain one or more of the following acidic compounds: $CO_2$, $H_2S$, mercaptans, COS, $SO_2$, $NO_2$, $CS_2$. In particular, the method according to the invention can be employed for absorbing acidic compounds contained in a gaseous effluent containing oxygen, for example flue gas. The oxygen content of the gaseous effluent can be above 500 ppm by volume, preferably above 0.5%, or even at least 1%, 3% or 5% by volume. In general, the oxygen content of the gaseous effluent remains below 20 vol. %. The flue gases are produced notably by combustion of hydrocarbons, of biogas, of coal a boiler or for a flue gas turbine, for example for producing electricity. These flue gases can comprise between 50 and 90% of nitrogen, and between 5 and 20% of carbon dioxide. The flue gases generally comprise at least 500 ppm by volume, preferably at least 1% by volume, or even 2%, 3% or 5% by volume of oxygen, up to a content that generally does not exceed 20 vol. % oxygen.

The application of an absorbent solution for deacidifying a gaseous effluent generally involves carrying out an absorption step followed by a regeneration step. The absorption step consists of contacting the gaseous effluent with the absorbent solution. During contact, the organic compounds provided with an amine function in the absorbent solution react with the acidic compounds contained in the effluent so as to obtain a gaseous effluent depleted of acidic compounds and an absorbent solution enriched with acidic compounds. The regeneration step consists notably of heating, and optionally of expanding, at least a proportion of the absorbent solution enriched with acidic compounds, in order to liberate the acidic compounds in gaseous form. The absorbent solution that has been regenerated, i.e. depleted of acidic compounds, is recycled to the absorption step.

The absorbent solution according to the invention comprises organic compounds in aqueous solution. In general, the organic compounds are amines, i.e. they comprise at least one amine function. The organic compounds can be of variable concentration, for example between 10 and 99 wt. %, preferably between 20 and 75 wt. %, or even between 20 and 50 wt. %, in the aqueous solution. The absorbent solution can contain between 1 and 90 wt. % of water, preferably between 25 and 80 wt. %, or even between 50 and 70 wt. % of water.

For example, the organic compounds are amines such as N,N,N',N',N''-pentamethyldiethylenetriamine or piperazine. For example, piperazine is used for treatment of natural gas and for decarbonation of flue gas.

The organic compounds can also be alkanolamines such as monoethanolamine (MEA), diethanolamine (DEA), methyldiethanolamine (MDEA), diisopropanolamine (DIPA) or diglycolamine. Preferably, MDEA and DEA are generally used for the deacidification of natural gas. MEA is more particularly used for the decarbonation of flue gas.

The organic compounds can also be salts of amino acids such as salts of glycine or of taurine, which are notably used for capture of $CO_2$ in flue gas.

Moreover, the absorbent solution according to the invention can contain compounds that physically absorb, at least partially, one or more acidic compounds of the gaseous effluent. For example, the absorbent solution can comprise between 5 and 50 wt. % of compounds that absorb physically, for example methanol, sulfolane or N-formyl morpholine.

Another advantage of the invention is that the use of the degradation-inhibiting additives according to the invention makes it possible to increase the concentration of amines commonly used by a person skilled in the art and thus increase process performance: increase in the capacity and rate of absorption of acidic compounds by the absorbent solution leading to a reduction in capital costs and operating costs of the industrial unit. In fact, as shown below in example 3, in the absence of degradation-inhibiting additives, the rate of degradation of the amines increases with increase in the concentration of amines. Thus, in the case for example of using an aqueous solution of MEA (monoethanolamine) for capture of $CO_2$ in flue gas, the concentration of MEA is generally limited to 30 wt. % to limit the degradation of this amine. It is understood here that the concentration of amine is defined as the percentage by weight in the water before absorption of $CO_2$. Thus, for example, an absorbent solution used for capture of $CO_2$ in flue gas and containing a degradation-inhibiting additive according to the invention can contain more than 30 wt. % and preferably more than 35 wt. % of MEA, a good value for the MEA concentration being at least equal to 39 wt. %.

Among the set of molecules belonging to the class of derivatives of pyrimidine and of triazine, at least one substituent of which contains a sulfur atom, the following degradation-inhibiting compounds are preferably used: 2-thiouracil (or 4-hydroxy-2-mercaptopyrimidine), 4-thiouracil (or 2-hydroxy-4-mercaptopyrimidine), 2-thiobarbituric acid (or 4,6-dihydroxypyrimidine-2-thiol), 2-mercaptopyrimidine, 3,4,5,6-tetrahydropyrimidine-2-thiol, 4,5-dihydro-4,4,6-trimethyl-2-pyrimidinethiol, 4-hydroxy-2-mercapto-6-methylpyrimidine, 2-mercapto-4-methylpyrimidine, 1,3,5-triazine-2,4,6-trithiol, salts of the aforementioned elements, as well as 4-methyl-2-(methylthio)pyrimidine.

The salts of the degradation-inhibiting compounds according to the invention can be obtained for example by neutralizing them with an alkali, alkaline-earth or metal or ammonium hydroxide or carbonate or with an amine present in the absorbent solution. In this case, it is at least one thiol function that will be neutralized.

The salts of the degradation-inhibiting compounds according to the invention can also be obtained for example by neutralizing them by means of an organic or inorganic acid. In this case, it is at least one nitrogen atom present in the ring that will be protonated.

The degradation-inhibiting compounds listed in the preceding paragraph are particularly well suited for preventing the degradation of amine in aqueous solution employed in a process for capture of $CO_2$ contained in flue gas.

To limit the degradation of an absorbent solution composed of amine, in particular of alkanolamine, for example monoethanolamine (MEA), in aqueous solution notably for capturing the $CO_2$ of flue gas, preferably one of the following compounds can be used: 2-thiobarbituric acid, 2-thiouracil, 3,4,5,6-tetrahydro-2-pyrimidinethiol or 1,3,5-triazine-2,4,6-trithiol, as well as their salts, for example sodium, potassium or ammonium salts, for example the sodium salts of 1,3,5-triazine-2,4,6-trithiol such as the sodium triple salt of 1,3,5-triazine-2,4,6-trithiol, also called sodium 1,3,5-triazine-2,4,6-trithiolate.

Preferably, according to the invention, 2-thiobarbituric acid, 2-thiouracil, 3,4,5,6-tetrahydro-2-pyrimidinethiol or the sodium triple salt of 1,3,5-triazine-2,4,6-trithiol is used for limiting the degradation of an amine, in particular MEA, in aqueous solution employed for deacidifying a gaseous effluent, notably in the context of capture of $CO_2$ contained in flue gas.

The absorbent solution according to the invention comprises an amount of degradation-inhibiting additives defined by the general formula described above. The absorbent solution can comprise one or more different degradation-inhibiting additives corresponding to said general formula. Moreover, in the absorbent solution, the degradation-inhibiting additives according to the invention can be associated with other degradation-inhibiting compounds of different chemical classes. According to the invention, the absorbent solution comprises between 5 ppm and 5 wt. % of degradation-inhibiting additives according to the invention, preferably from 50 ppm to 2 wt. %, and an excellent content of degradation-inhibiting additives in the solution is between 100 ppm and 1 wt. %.

The examples presented below provide comparison and illustration of the performance of the degradation-inhibiting additives according to the invention, in terms of reducing the degradation of the amines in aqueous solution, reducing the emissions of volatile degradation compounds and the possibility of increasing the concentration of amines without increasing their degradation.

EXAMPLE 1

The amines in the absorbent solution can be degraded when used according to the invention, causing consumption of the amine.

The tests of degradation of an amine in aqueous solution are carried out according to the following procedure.

100 g of solution of MEA (monoethanolamine) 30 wt. % in deionized water is put in a glass reactor equipped with a condenser to prevent evaporation of water. The reactor is heated at 80° C. in an electric heating block. The solution is stirred at 1000 rev/min by a magnetized bar. The presence of counterblades prevents formation of a vortex. A gas is brought into contact with the solution by means of a plunger tube for 7 days at atmospheric pressure. Depending on the tests, the nature of the gas brought into contact with the solution can be varied. Moreover, the tests are conducted either in the absence or in the presence of different degradation-inhibiting additives incorporated in the aqueous solution of amine at 0.25 wt. %.

When the test is carried out only in the presence of $CO_2$ and in the absence of oxygen, the gas brought into contact with the solution is a mixture of 7 Nl/h of nitrogen and 0.033 Nl/h of $CO_2$ produced in a mixing chamber. In this case, the gas only comprises $CO_2$ and nitrogen.

When the test is carried out in the presence of $CO_2$ and oxygen, the gas brought into contact with the solution is a mixture of 7 Nl/h of atmospheric air, i.e. of unpurified ambient air, and of 0.033 Nl/h of $CO_2$ produced in a mixing chamber. In this case, the gas contains $CO_2$, nitrogen and oxygen, the oxygen content in the gas being about 21%.

The solution thus degraded is analyzed by gas chromatography at the end of the test. The chromatographic method uses a polar column, a carrier gas, helium, an internal standard, triethylene glycol and FID (Flame Induced Detection) detection. This analysis is able to determine the residual concentration of MEA and therefore the degree of degradation defined by:

$$\mathrm{degree\_of\_degredation} = \left(1 - \frac{[MEA]\,\mathrm{final}}{[MEA]\,\mathrm{initial}}\right)*100$$

Table 1 gives the degrees of degradation of an aqueous solution of MEA (monoethanolamine) 30 wt. %, in the absence or in the presence of a degradation inhibitor, submitted to a gas containing nitrogen, $CO_2$ and containing or not containing oxygen:

- Case No. 1: without oxygen and without additive
- Case No. 2: in the presence of oxygen and without additive
- Case No. 3: in the presence of oxygen and in the presence of a conventional antioxygen additive, sodium sulfite ($Na_2SO_3$).
- Case No. 4: in the presence of oxygen and in the presence of an additive according to the invention, 2-thiobarbituric acid.
- Case No. 5: in the presence of oxygen and in the presence of an additive according to the invention, 2-thiouracil.
- Case No. 6: in the presence of oxygen and in the presence of an additive according to the invention, 3,4,5,6-tetrahydro-2-pyrimidinethiol.
- Case No. 7: in the presence of oxygen and in the presence of an additive according to the invention, the sodium triple salt of 1,3,5-triazine-2,4,6-trithiol.

TABLE 1 comparison of the degrees of degradation of MEA 30 wt. % obtained in water at 80° C. in different cases.

| CASE | $O_2$ content | Name of the additive | Degree of degradation |
|---|---|---|---|
| 1 | 0% | — | <3% |
| 2 | 21% | — | 70% |
| 3 | 21% | sodium sulfite ($Na_2SO_3$) | 71% |
| 4 | 21% | 2-thiobarbituric acid | <3% |
| 5 | 21% | 2-thiouracil | <3% |
| 6 | 21% | 3,4,5,6-tetrahydro-2-pyrimidinethiol | <3% |
| 7 | 21% | sodium triple salt of 1,3,5-triazine-2,4,6-trithiol | <3% |

It can clearly be seen that:
1. the solution of MEA is not degraded in the presence of $CO_2$ alone, in the absence of oxygen
2. the degradation of MEA is attributable to the presence of oxygen
3. in the presence of a conventional antioxygen additive such as sodium sulfite, the degradation of MEA in the presence of oxygen is not decreased 4. in the presence of additives according to the invention, the degradation of MEA is brought to the same level as that found in the absence of oxygen, i.e. regarded as zero as it is less than the uncertainty of measurement, which is 3%.

In conclusion, the additives according to the invention effectively counteract the effect of oxygen on the degradation of MEA.

EXAMPLE 2

In particular, amines can be degraded by oxygen, causing the formation of volatile products, which are entrained in the gaseous effluents of the process. Thus, for example in the case of post-combustion treatment of flue gas in a method using an aqueous solution of MEA, large amounts of ammonia are formed. The ammonia thus formed is entrained into the atmosphere with the treated flue gas, which poses problems with respect to protection of the environment.

FIG. 1 presents monitoring of the concentration of ammonia in the gas leaving the reactor in cases 2, 3, 4, 5, 6 and 7 defined in example 1. [A] corresponds to the ammonia concentration in ppm by volume in the gas leaving the reactor, t represents time expressed in days. Cases 2, 3, 4, 5, 6 and 7 are represented respectively by curve 2 with a solid line, curve 3 with white squares, curve 4 with white triangles, curve 5 with crosses, curve 6 with white diamonds and curve 7 with black circles.

The ammonia concentration in the gas leaving the reactor is determined by line analysis by Fourier transform infrared spectrometry.

In the case of the degradation-inhibiting additives according to the invention, the $NH_3$ content is always very low compared with that obtained in the case of a conventional antioxygen additive (see curve 3), sodium sulfite and that obtained in the absence of inhibitor (see curve 2).

This example therefore clearly shows that the degradation-inhibiting additives according to the invention are effective for reducing the emissions of volatile degradation compounds. Consequently, in an industrial process using an absorbent solution containing degradation-inhibiting additives according to the invention, the emissions of volatile compounds at the top of the absorber will be much lower than in the absence of degradation-inhibiting additives.

EXAMPLE 3

This example shows that the use of the amine degradation-inhibiting additives makes it possible to increase the concentration of amine without increasing degradation. This example gives the results obtained with an aqueous solution of MEA at 40 wt. %.

The tests of degradation of an amine in aqueous solution are carried out according to the following procedure.

100 g of solution of MEA 40 wt. % in deionized water is put in a glass reactor equipped with a condenser to prevent evaporation of water. The reactor is heated at 80° C. in an electric heating block. The solution is stirred at 1000 rev/min by a magnetized bar. The presence of counterblades prevents formation of a vortex. A gas is brought into contact with the solution by means of a plunger tube for 7 days at atmospheric pressure. The tests are carried out either in the absence or in the presence of a degradation-inhibiting additive incorporated in the aqueous solution of amine at 0.25 wt. %.

The test is carried out in the presence of $CO_2$ and oxygen: the gas brought into contact with the solution is a mixture of 7 Nl/h of atmospheric air, i.e. of unpurified ambient air, and of 0.033 Nl/h of $CO_2$ produced in a mixing chamber. The gas therefore contains $CO_2$, nitrogen and oxygen, the oxygen content in the gas being about 21%.

The solution thus degraded is analyzed by gas chromatography at the end of the test. The chromatographic method uses a polar column, a carrier gas, helium, an internal standard, triethylene glycol and FID (Flame Induced Detection) detection. This analysis makes it possible to determine the residual concentration of MEA.

An average rate of degradation over the duration of the test can therefore be calculated:

$$\text{average\_rate\_of\_degredation} = \frac{[MEA]_{initial} - [MEA]_{final}}{\text{test\_duration}} * \text{mass\_of\_solutions}$$

A degree of degradation can also be calculated:

$$\text{degree\_of\_degradation} = \left(1 - \frac{[MEA]\,\text{final}}{[MEA]\,\text{initial}}\right) * 100$$

Table 2 gives the average rates of degradation of MEA obtained in the same conditions in case No. 8 of a MEA 40 wt. % without additive and case No. 2 of a MEA 30 wt. % without additive defined in example 1.

TABLE 2 comparison of the average rates of degradation of MEA 30 and 40 wt. % in the absence of a degradation-inhibiting additive according to the invention.

| CASE | $O_2$ content | [MEA] in wt. % | Average rate of degradation (g/day) |
|---|---|---|---|
| 2 | 21% | 30% | 2.99 |
| 8 | 21% | 40% | 3.72 |

Table 2 provides good confirmation that an aqueous solution of MEA 40 wt. % degrades more quickly than a solution of MEA 30 wt. %. Thus, for one and the same duration, the mass of MEA degraded is greater in the case of an aqueous solution of MEA 40 wt. %.

Table 3 gives the degrees of degradation of an aqueous solution of MEA 40 wt. %, in the absence or in the presence of different degradation-inhibiting additives:

Case No. 8: without additive

Case No. 9: in the presence of an additive according to the invention, 3,4,5,6-tetrahydro-2-pyrimidinethiol

TABLE 3 comparison of the degrees of degradation of MEA 40 wt. % obtained in water at 80° C. in the absence and in the presence of different degradation-inhibiting additives according to the invention.

| CASE | $O_2$ content | Name of the additive | Degree of degradation |
|---|---|---|---|
| 8 | 21% | — | 66% |
| 9 | 21% | 3,4,5,6-tetrahydro-2-pyrimidinethiol | <3% |

It can clearly be seen that in the presence of an additive according to the invention, the degradation of MEA at 40 wt. % in water can be regarded as zero as it is less than the uncertainty of measurement, which is 3%.

In conclusion, in the case of MEA, the additives according to the invention make it possible to increase the concentration of amine commonly used by a person skilled in the art without increasing the degradation of the amine.

EXAMPLE 4

This example shows that the use of the amine degradation-inhibiting additives makes it possible to increase the amine concentration without increasing the emissions of volatile degradation products. This example gives the results obtained with an aqueous solution of MEA at 40 wt. %.

FIG. 2 presents the monitoring of the concentration of ammonia in the gas leaving the reactor in cases 8 and 9 defined in example 3. [A] corresponds to the ammonia concentration in ppm by volume in the gas leaving the reactor, t represents time expressed in days. Cases 8 and 9 are represented respectively by curve 8 with white circles and curve 9 with black diamonds.

The ammonia concentration in the gas leaving the reactor is determined by line analysis by Fourier transform infrared spectrometry.

In the case of the degradation-inhibiting additive according to the invention, the $NH_3$ content is below 10 ppm throughout the test whereas it soon exceeds 2000 ppm without degradation-inhibiting additive. It can clearly be seen that in the presence of an additive according to the invention, the emissions of ammonia associated with the degradation of MEA at 40 wt. % in water are reduced considerably.

This example therefore clearly shows, in the case of MEA, that the degradation-inhibiting additives according to the invention make it possible to increase the amine concentration commonly used by a person skilled in the art without increasing the emissions of ammonia.

Consequently, in an industrial process using an absorbent solution containing degradation-inhibiting additives according to the invention, the emissions of volatile compounds at the top of the absorber will be much lower than in the absence of inhibiting additives even if the amine concentration is increased relative to the concentration generally used by a person skilled in the art.

The invention claimed is:

1. A method of absorbing acidic compounds contained in a gaseous effluent, comprising:
    bringing a gaseous effluent containing acidic compounds into contact with a solution comprising:
    a) at least one amine selected from the group consisting of N,N,N',N',N''-pentamethyldiethylenetriamine, piperazine, monoethanolamine, diethanolamine, methyldiethanolamine, diisopropanolamine, diglycolamine, a glycine salt and a taurine salt,
    b) water,
    c) at least one degradation-inhibiting compound for limiting the degradation of said amine, said degradation-inhibiting compound corresponding to one of the following general formulas:

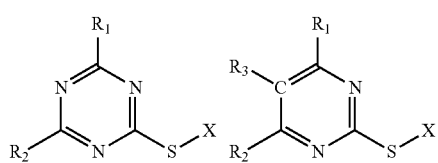

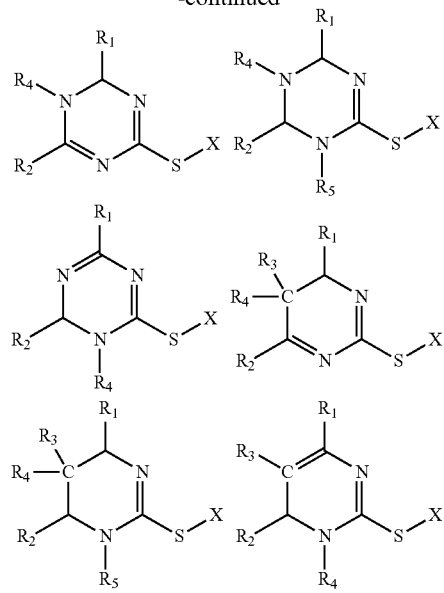

in which X is selected from
    a hydrogen atom,
    an alkali or alkaline-earth element,
    a monovalent or multivalent metal,
    $NH_4^+$ or ammonium cation resulting from the protonation of an amine function,
    a phosphonium cation,
in which each of the radicals $R_1$, $R_2$ and $R_3$ is selected independently from:
    a hydrogen atom,
    a hydrocarbon radical comprising 1 to 12 carbon atoms,
    a radical

in which W is selected from a sulfur atom and an oxygen atom and Y is selected from:
    a hydrogen atom,
    a hydrocarbon radical comprising 1 to 12 carbon atoms,
    an alkali or alkaline-earth element,
    a monovalent or multivalent metal,
    $NH_4^+$ or an ammonium cation resulting from the protonation of an amine function,
    a phosphonium cation,
and in which each of the radicals $R_4$ and $R_5$ is selected independently from:
    a hydrogen atom,
    a hydrocarbon radical comprising 1 to 12 carbon atoms.

2. The method according to claim 1, in which the solution comprises between 10 and 99 wt. % of amine, between 1 and 90 wt. % of water and between 5 ppm and 5 wt. % of degradation-inhibiting compound.

3. The method according to claim 1, in which the degradation-inhibiting compound is selected from the group containing: 2-thiouracil, a salt of 2-thiouracil, 4-thiouracil, a salt of 4-thiouracil, 2-thiobarbituric, a salt of 2-thiobarbituric, 2-mercaptopyrimidine, a salt of 2-mercaptopyrimidine, 3,4,5,6-tetrahydropyrimidine-2-thiol, a salt of 3,4,5,6-tetrahydropyrimidine-2-thiol, 4,5-dihydro-4,4,6-trimethyl-2-pyrimidinethiol, a salt of 4,5-dihydro-4,4,6-trimethyl-2- pyrimidinethiol, 4-hydroxy-2-mercapto-6-methylpyrimidine, a salt of 4-hydroxy-2-mercapto-6-methylpyrimidine, 2-mercapto-4-methylpyrimidine, a salt of 2-mercapto-4-methylpyrimidine, 1,3,5-triazine-2,4,6-trithiol, a salt of 1,3,5-triazine-2,4,6-trithiol, and 4-methyl-2-(methylthio)pyrimidine.

4. The method according to claim 1, in which the amine is monoethanolamine and in which the degradation-inhibiting compound is selected from 2-thiobarbituric acid, 2-thiouracil, 3,4,5,6-tetrahydro-2-pyrimidinethiol and the sodium triple salt of 1,3,5-triazine-2,4,6-trithiol.

5. The method according to claim 1, wherein the solution comprises at least 39 wt. % of monoethanolamine.

6. The method according to claim 1, wherein the gaseous effluent containing acidic compounds is selected from the group consisting of natural gas, flue gas, synthesis gases, refinery gases, gases obtained at the end of the Claus process, gases from fermentation of biomass, gases from cement works and incinerator flue gas.

7. The method according to claim 6, in which the gaseous effluent containing acidic compounds comprises at least 500 ppm by volume of oxygen.

8. The method according to claim 1, in which the degradation-inhibiting compound is selected from the group containing: 2-thiouracil, a salt of 2-thiouracil, 2-thiobarbituric acid, a salt of 2-thiobarbituric acid, 2-mercaptopyrimidine, a salt of 2-mercaptopyrimidine, 4-hydroxy-2-mercapto-6-methylpyrimidine, a salt of 4-hydroxy-2-mercapto-6-methylpyrimidine, 2-mercapto-4-methylpyrimidine, a salt of 2-mercapto-4-methylpyrimidine, and 4-methyl-2-(methylthio)pyrimidine.

9. The method according to claim 1, in which the amine is monoethanolamine and in which the degradation-inhibiting compound is selected from 2-thiobarbituric acid, and 2-thiouracil.

10. The method according to claim 1, in which the degradation-inhibiting compound corresponds to one of the following general formulas:

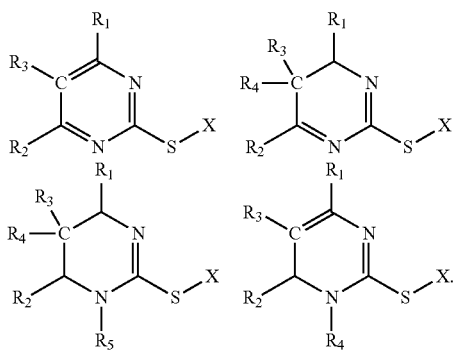

11. The method according to claim 9, in which the solution comprises between 10 and 99 wt. % of amine, between 1 and 90 wt. % of water and between 5 ppm and 5 wt. % of degradation-inhibiting compound.

12. The method according to claim 9, wherein the solution at least 39 wt. % of monoethanolamine.

13. The method according to claim 9, wherein the gaseous effluent containing acidic compounds is selected from the group consisting of natural gas, flue gas, synthesis gases, refinery gases, gases obtained at the end of the Claus process, gases from fermentation of biomass, gases from cement works and incinerator flue gas.

14. The method to claim 13, in which the gaseous effluent containing acidic compounds comprises at least 500 ppm by volume of oxygen.

15. A method of absorbing acidic compounds contained in a gaseous effluent, comprising:
bringing a gaseous effluent containing acidic compounds into contact with a solution comprising:
a) at least one amine selected from the group consisting of N,N,N',N',N"-pentamethyldiethylenetriamine, piperazine, monoethanolamine, diethanolamine, methyldiethanolamine, diisopropanolamine, diglycolamine, a glycine salt and a taurine salt,
b) water,
c) at least one degradation-inhibiting compound for limiting the degradation of said amine, said degradation-inhibiting compound corresponding to one of the following general formulas:

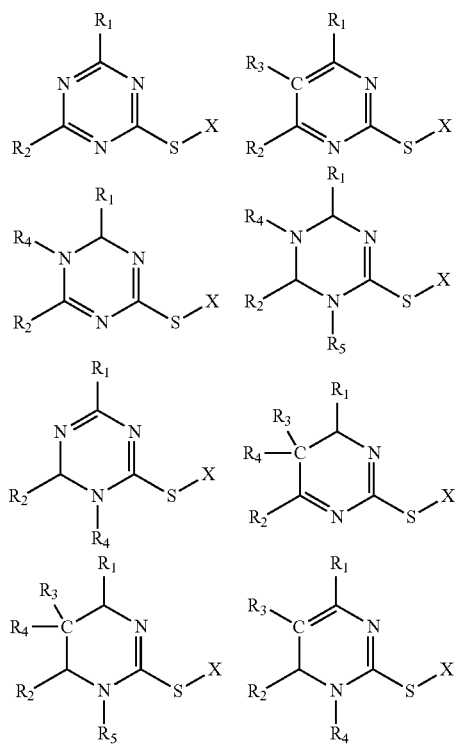

in which X is selected from
a hydrogen atom,
an alkali or alkaline-earth element,
a monovalent or multivalent metal,
$NH_4^+$ or an ammonium cation resulting from the protonation of an amine function,
a phosphonium cation,
in which each of the radicals $R_1$, $R_2$ and $R_3$ is selected independently from:
a hydrogen atom,
a hydrocarbon radical comprising 1 to 12 carbon atoms
a radical

in which W is selected from a sulfur atom and an oxygen atom and Y is selected from:

a hydrogen atom, a hydrocarbon radical comprising 1 to 12 carbon atoms, an alkali or alkaline-earth element, a monovalent or multivalent metal, $NH_4^+$ or an ammonium cation resulting from the protonation of an amine function, a phosphonium cation, in which at least one of the radicals $R_1$, $R_2$, $R_3$, X and Y is a hydrocarbon group containing between 1 and 12 carbon atoms or a hydrocarbon group containing between 1 and 12 carbon atoms joined to at least one selected from the group consisting of a heteroatom and a halogen, and in which each of the radicals $R_4$ and $R_5$ is selected independently from:

a hydrogen atom, a hydrocarbon radical comprising 1 to 12 carbon atoms.

16. A method of absorbing acidic compounds contained in a gaseous effluent, comprising:

bringing a gaseous effluent containing acidic compounds into contact with a solution comprising:

a) at least one amine selected from the group consisting of N,N,N',N',N''-pentamethyldiethylenetriamine, piperazine, monoethanolamine, diethanolamine, methyldiethanolamine, diisopropanolamine, diglycolamine, a glycine salt and a taurine salt, b) water, c) at least one degradation-inhibiting compound for limiting the degradation of said amine, said degradation-inhibiting compound corresponding to one of the following general formulas:

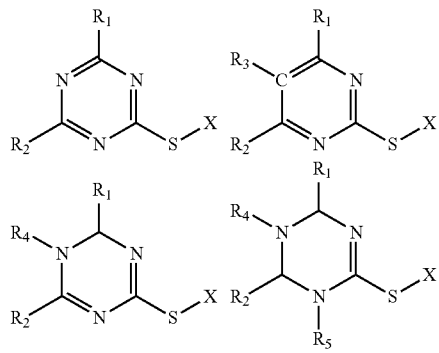

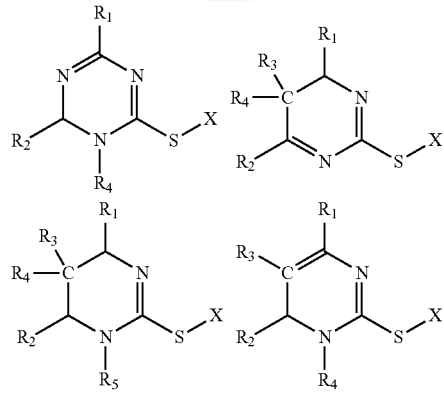

in which X is selected from a hydrogen atom, an alkali or alkaline-earth element, a monovalent or multivalent metal, $NH_4^+$ or an ammonium cation resulting from the protonation of an amine function, a phosphonium cation, in which each of the radicals $R_1$ $R_2$ and $R_3$ is selected independently from:

a hydrogen atom, a hydrocarbon radical comprising 1 to 12 carbon atoms a radical

in which W is selected from a sulfur atom and an oxygen atom and Y is selected from:

a hydrogen atom, a hydrocarbon radical comprising 1 to 12 carbon atoms, an alkali or alkaline-earth element, a monovalent or multivalent metal, $NH_4^+$ or an ammonium cation resulting from the protonation of an amine function, a phosphonium cation, in which at least one of the radicals $R_1$, $R_2$, $R_3$, X and Y is a substituted hydrocarbon group containing between 1 and 12 carbon atoms and further comprises by substitution at least one function selected from the group: a hydroxyl function, a ketone function, a carboxyl function and a nitrile function, and in which each of the radicals $R_4$ and $R_5$ is selected independently from:

a hydrogen atom, a hydrocarbon radical comprising 1 to 12 carbon atoms.

* * * * *